(12) United States Patent
Lechot et al.

(10) Patent No.: US 10,105,148 B2
(45) Date of Patent: Oct. 23, 2018

(54) ACETABULAR REAMER ASSEMBLY

(71) Applicant: Incipio Devices SA, St-Blaise (CH)

(72) Inventors: André Lechot, Orvin (CH); Fabrice Chenaux, Montmollin (CH)

(73) Assignee: Incipio Devices SA, St. Blaise (CH)

( * ) Notice: Subject to any disclaimer, the term of this patent is extended or adjusted under 35 U.S.C. 154(b) by 407 days.

(21) Appl. No.: 14/894,573

(22) PCT Filed: May 30, 2014

(86) PCT No.: PCT/IB2014/000902
§ 371 (c)(1),
(2) Date: Nov. 30, 2015

(87) PCT Pub. No.: WO2014/191826
PCT Pub. Date: Dec. 4, 2014

(65) Prior Publication Data
US 2016/0135820 A1   May 19, 2016
US 2018/0028197 A9   Feb. 1, 2018

Related U.S. Application Data

(60) Provisional application No. 61/829,269, filed on May 31, 2013.

(51) Int. Cl.
*A61B 17/00* (2006.01)
*A61B 17/16* (2006.01)

(52) U.S. Cl.
CPC ...... *A61B 17/1666* (2013.01); *A61B 17/1615* (2013.01); *A61B 17/1642* (2013.01)

(58) Field of Classification Search
None
See application file for complete search history.

(56) References Cited

U.S. PATENT DOCUMENTS

| 5,462,548 A | 10/1995 | Pappas et al. |
| 5,755,719 A | 5/1998 | Frieze et al. |
| 5,897,558 A | 4/1999 | Frieze et al. |

(Continued)

FOREIGN PATENT DOCUMENTS

WO   WO 2004/024007 A1   3/2004

OTHER PUBLICATIONS

PCT/IB2014/000902, International Search Report, dated Sep. 26, 2014.

*Primary Examiner* — Sameh Boles
(74) *Attorney, Agent, or Firm* — Da Vinci Partners LLC; John Moetteli

(57) ABSTRACT

The present invention provides a surgical reamer (10), surgical reamer system, and kit including a surgical reamer. The surgical reamer has a domed shell (12) extending from the apex to the rim (13), a rotation axis (17), cutting teeth (14) disposed around the domed shell wherein a first connecting bar (15) having a first longitudinal axis and a first diameter is located on the inside surface of the domed shell, with its first longitudinal axis and a first diameter is located on the inside surface of the domed shell, with its first longitudinal axis being adjacent or closely adjacent to the rim and in which a second connecting bar (16) having a second longitudinal axis and a second diameter is located on the inside surface of the domed shell and spaced apart from the first connecting bar.

7 Claims, 10 Drawing Sheets

(56) References Cited

U.S. PATENT DOCUMENTS

| | | |
|---|---|---|
| 6,283,972 B1 | 9/2001 | Riley |
| 7,901,405 B2 | 3/2011 | White et al. |
| 2004/0167528 A1 | 8/2004 | Schantz |
| 2006/0094955 A1 | 5/2006 | Marquardt et al. |
| 2006/0195110 A1 | 8/2006 | White et al. |
| 2008/0161813 A1* | 7/2008 | Sherry ............... A61B 17/1666 |
| | | 606/81 |

* cited by examiner

ACETABULAR REAMER ASSEMBLY

CROSS REFERENCE TO RELATED APPLICATION

This application is the National Stage of International Application No. PCT/IB2014/000902, filed May 30, 2014, which claims benefit under 35 USC § 119(a), to U.S. provisional patent application Ser. No. 61/829,269, filed May 31, 2013.

This application claims the benefit of U.S. Provisional Application No. 61/829,269, filed May 31, 2013, entitled: "Acetabular Reamer Assembly", the contents of which are incorporated herein by reference thereto.

COPYRIGHT & LEGAL NOTICE

A portion of the disclosure of this patent document contains material which is subject to copyright protection. The Applicant has no objection to the facsimile reproduction by anyone of the patent document or the patent disclosure as it appears in the Patent and Trademark Office patent file or records, but otherwise reserves all copyright rights whatsoever. Further, no references to third party patents or articles made herein is to be construed as an admission that the present invention is not entitled to antedate such material by virtue of prior invention.

FIELD OF THE INVENTION

This invention relates to a surgical reamer, method, kit, surgical system and surgical apparatus for use in preparing a bone or bone cavity for subsequent implantation of a joint replacement prosthesis. The invention has particular application to a surgical reamer for enlarging and shaping a cavity within a bone for the implantation of the component of a joint prosthesis.

BACKGROUND OF THE INVENTION

A natural joint may undergo degenerative changes due to a variety of etiologies. When these changes are far advanced and irreversible, it is necessary at times to replace the natural joint with a prosthesis. When implantation of such a prosthesis becomes necessary, the head of the natural bone is resected and a cavity is created within the intramedullary canal of the host bone for accepting and supporting the prosthesis. The acetabulum is enlarged and shaped with acetabular reamers for accepting the prosthesis. Typical types of acetabular reamers are described in U.S. Pat. Nos. 5,462,548, 5,755,719 and 5,897,558.

SUMMARY OF THE INVENTION

The present invention provides a surgical reamer having a domed shell extending from the apex to the rim, a rotation axis, and cutting teeth disposed around the domed shell. A first connecting bar having a first longitudinal axis and a first diameter is located on the inside surface of the domed shell with its first longitudinal axis being adjacent or closely adjacent to the rim. A second connecting bar having a second longitudinal axis and a second diameter is located on the inside surface of the domed shell and spaced apart from the first connecting bar.

In a variant, the first connecting bar has two centering features, each one having a face that is symmetrically spaced apart with the other from the rotation axis of the domed shell.

In yet another variant, the space between the first and the second connecting bars is equal to the sum of the first and second diameters of the bars divided by two.

In yet a further variant, the second connecting bar is perpendicular to the first connecting bar.

In yet another aspect, the connecting bars are solid or hollow, and have a cross-section that is round, square, rectangular, elliptical, round with flats or hexagonal.

In yet a further aspect, an item of information is displayed on the first connecting bar.

In another variant, the invention includes surgical protocols using the reamer of the present invention. A surgical protocol includes reaming a joint with the surgical reamer and implanting a joint prosthesis.

In yet a further variant, the step of implanting includes pre-operatively planning and evaluating a target area through X-ray and/or other imaging system evaluation, acetabular preparation, assessment of bone stock, level of interference and proper amount of under-reaming, trial evaluation of a restoration cup following the reaming step, implanting a restoration cup, and implanting other prosthesis components.

In yet another variant, the invention described herein includes a kit having one or more variants of the surgical reamer described herein. The kit also includes optional accessories. The accessories are selected from one or more of the following: a reamer handle, a reamer actuator, a positioning assembly, a variety of different diameter and length bone screws, a variety of different size liners, a variety of different size locking rings, a variety of sized shells, a variety of different size liner shells (e.g. polyethylene shells), and a variety of prosthesis implantation tools.

In yet a further variant, the kit also includes prosthesis implant components, and disposables related thereto.

In yet an alternate variant, the surgical system comprising the surgical reamer and variants described herein. The surgical system includes a surgical reamer driver, and surgical operating suite components and the other components described herein.

These and other aspects of the invention are further described in the drawings, and the detailed description below.

Those skilled in the art will appreciate that elements in the Figures are illustrated for simplicity and clarity and have not necessarily been drawn to scale. For example, dimensions may be exaggerated relative to other elements to help improve understanding of the invention and its variants. Furthermore, when the terms 'first', 'second', and the like are used herein, their use is intended for distinguishing between similar elements and not necessarily for describing a sequential or chronological order. Moreover, relative terms like 'front', 'back', 'top' and 'bottom', and the like in the Description and/or in the claims are not necessarily used for describing exclusive relative position. Those skilled in the art will therefore understand that such terms may be interchangeable with other terms, and that the variants described herein are capable of operating in other orientations than those explicitly illustrated or otherwise described.

DETAILED DESCRIPTION OF THE PREFERRED EMBODIMENT(S)

The following description is not intended to limit the scope of the invention in any way as they are exemplary in nature, serving to describe the best mode of the invention known the inventors as of the filing date hereof. Consequently, changes may be made in the arrangement and/or function of any of the elements described in the exemplary variants disclosed herein without departing from the spirit and scope of the invention.

Figure 1A:
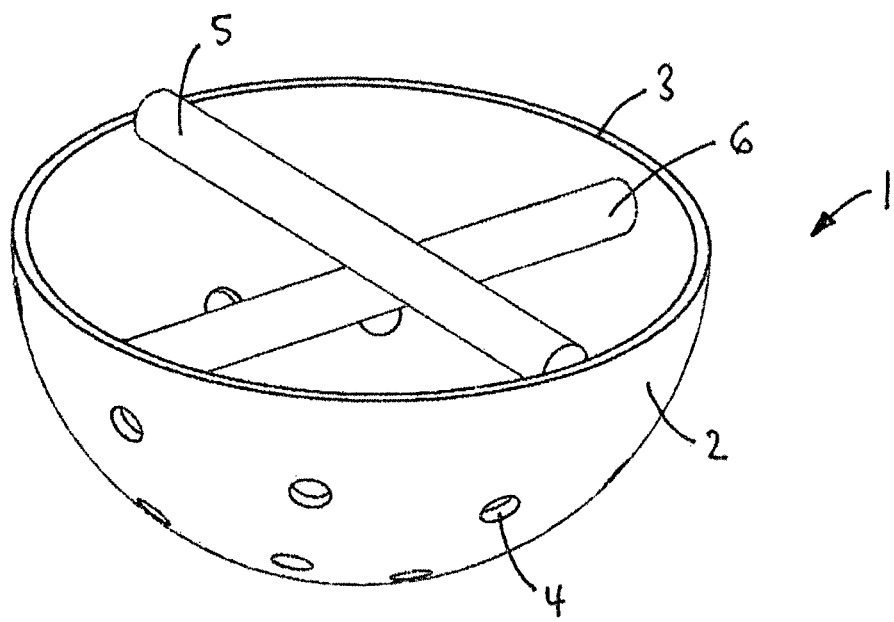
FIG. 1A is a perspective view of a variant of the acetabular reamer.
Figure 1B:
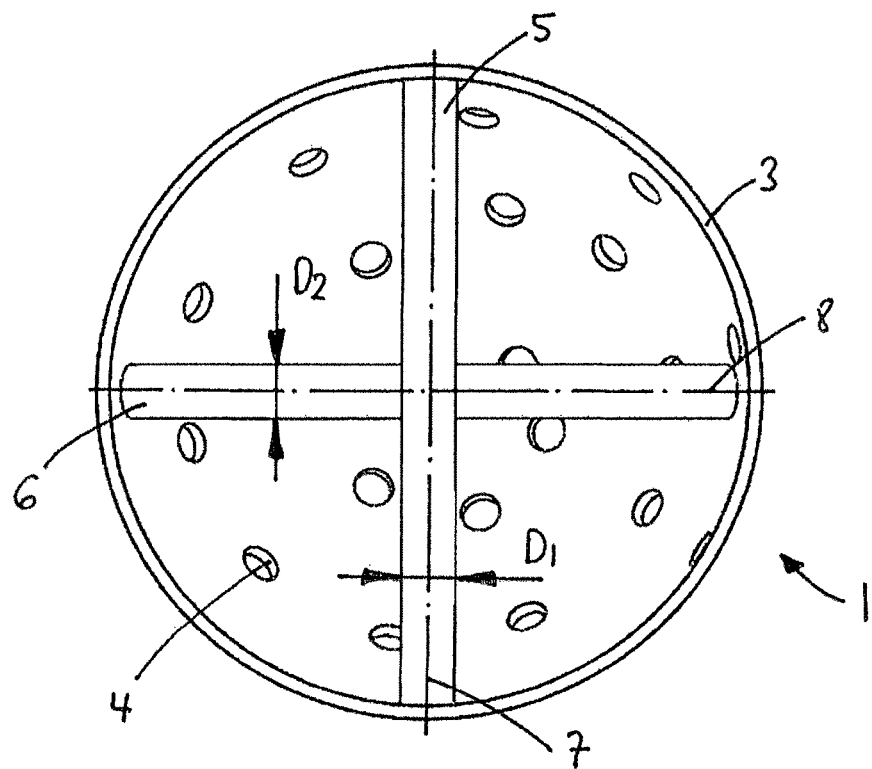
FIG. 1B is a top view of a variant of the acetabular reamer.

Referring to FIGS. 1A and 1B, the acetabular reamer 10 comprises a domed shell portion 12 having a rim 13. The domed shell 12 has cutting teeth 14 disposed all around the domed shell in order to insure an even reaming of a spherical shape when rotated around its main axis. The cutting teeth 14 are located at a variety of positions on the surface of domed shell portion 12. A first connecting bar 15 having a longitudinal axis 17 and a diameter D1 is located on the inside surface of the domed shell 12, with its longitudinal axis 17 being adjacent or closely adjacent to the rim 13 of the domed shell. A second connecting bar 16 having a longitudinal axis 18 and a diameter D2 is located on the inside surface of the domed shell 12 and positioned preferably perpendicular to the first connecting bar 15. The second connecting bar 16 is spaced apart from the first connecting bar 15.

Figure 1C:
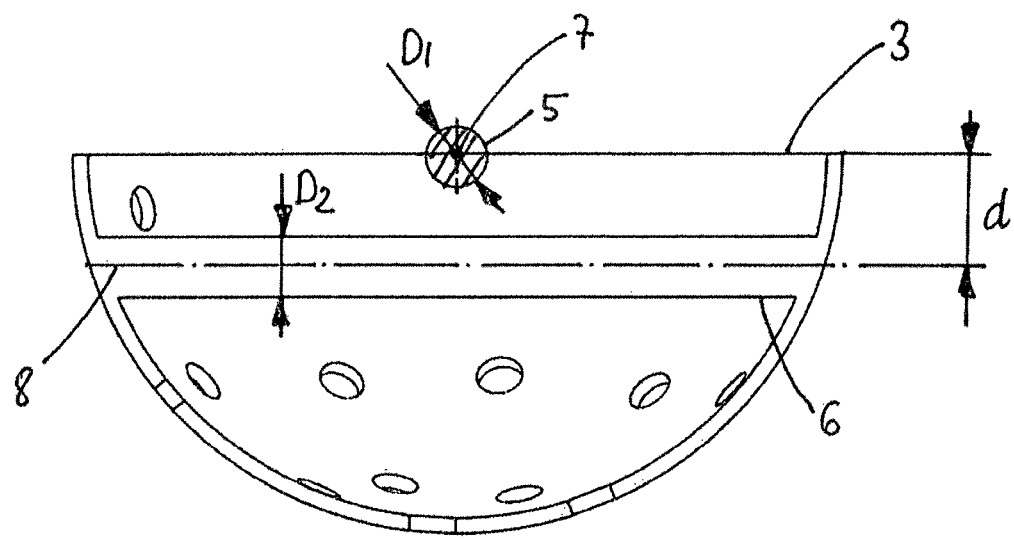
FIG. 1C is a cross-section view of a variant of the acetabular reamer.
Figure 2:
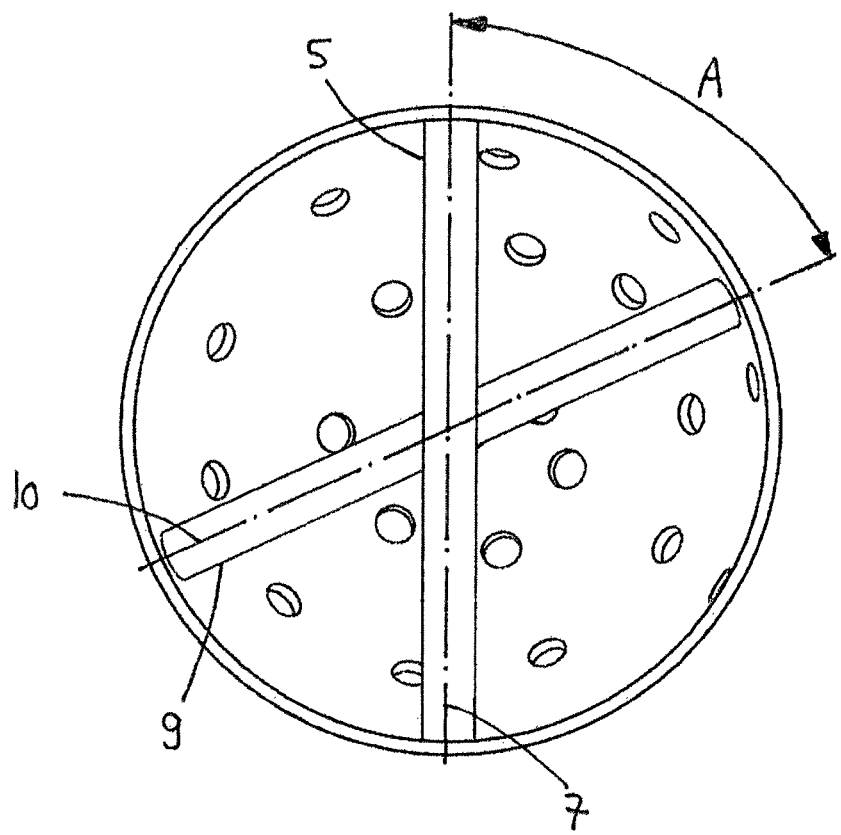
FIG. 2 is a top view of a different variant of the acetabular reamer.

In one of the variants of FIG. 1C the distance d between the longitudinal axis 17 of the first connecting bar 15 and the longitudinal axis 18 of the second connecting bar 16 is larger than (D1+D2)/2 or approximations thereof. In a different variant, the distanced is equal to (D1+D2)/2. It appreciated that a variety of distances d are used in variants of the invention. In a different variant shown in FIG. 2, the angle A between the longitudinal axis 17 of the first connecting bar 15 and the longitudinal axis 20 of the second connecting bar 19 is less than 90°.

Figure 3:
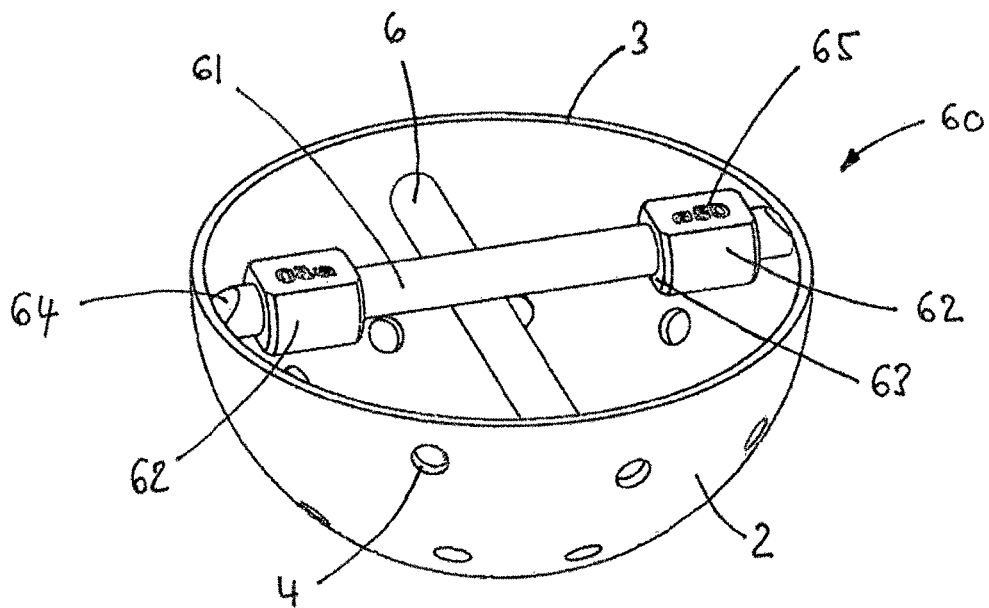
FIG. 3 is a perspective view of another different variant of the acetabular reamer.

In the other different variant of FIG. 3, the first connecting bar 61, having a diameter D1, has two centering features 62 having a larger diameter than the diameter D1. Both centering features have a face 63 that is symmetrically spaced apart with the other from the rotation axis of the domed shell. Both faces 63 center the acetabular reamer once connected to the reamer driver. Optionally chamfers 64 may be cut at the extremities of the connecting bar 61 to suppress sharp edges. Still further, optionally, marking or engraving of information like cutting size of the reamer 65 may be realized on the features 62.

Figure 4A:
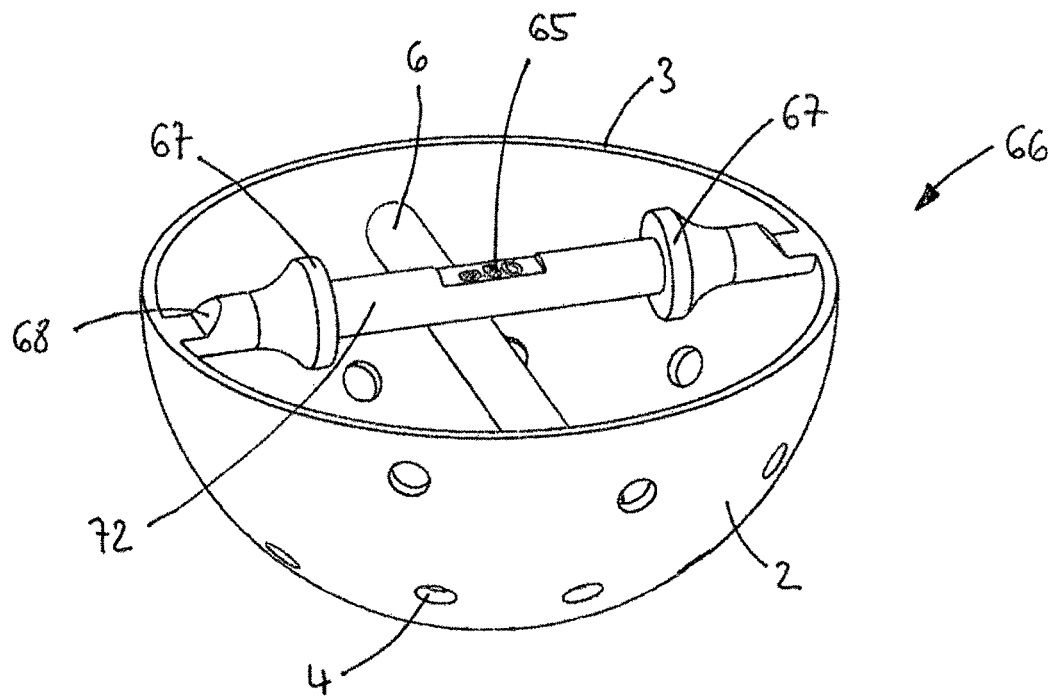
FIG. 4A is a perspective view of the preferred variant of the acetabular reamer.

In the variant of FIG. 4A, the first connecting bar 72, having a diameter D1, has two centering tapered features 67 having a larger diameter than the diameter D1. Both centering tapered features 67 have the same function as described above in FIG. 3. Flats and tapers 68 are cut at both extremities of the connecting bar 72 to suppress sharp edges. The cutting size of the reamer 65 is marked or engraved on the center of the connecting bar 72.

Figure 4B:
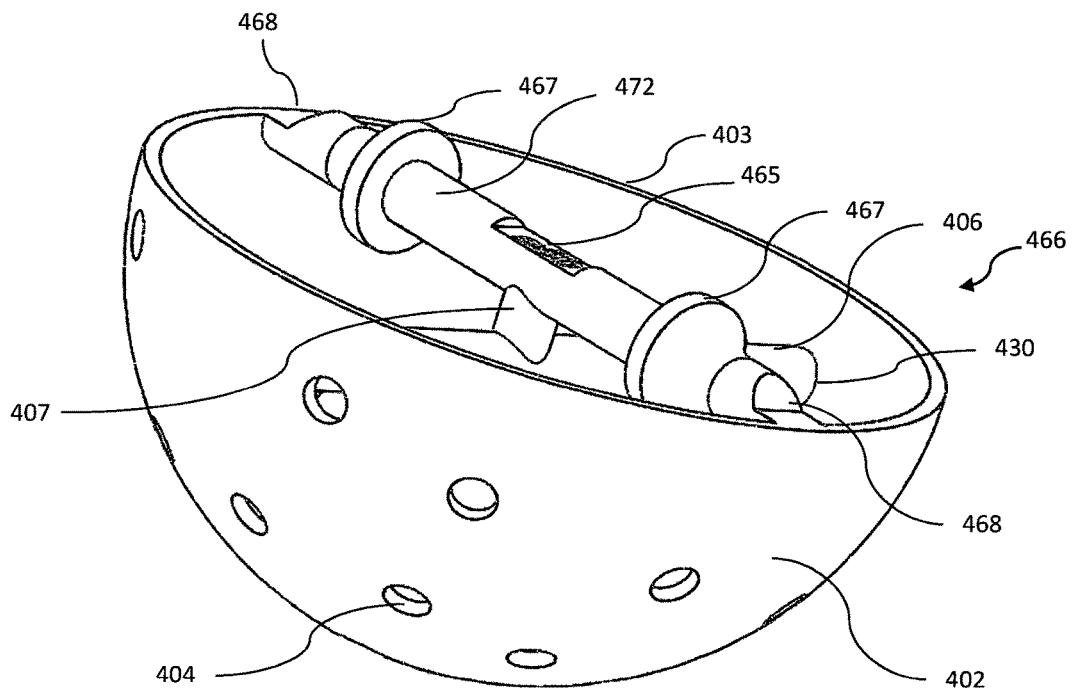
FIG. 4B is a perspective view on another variant of the acetabular reamer.
Figure 4C:
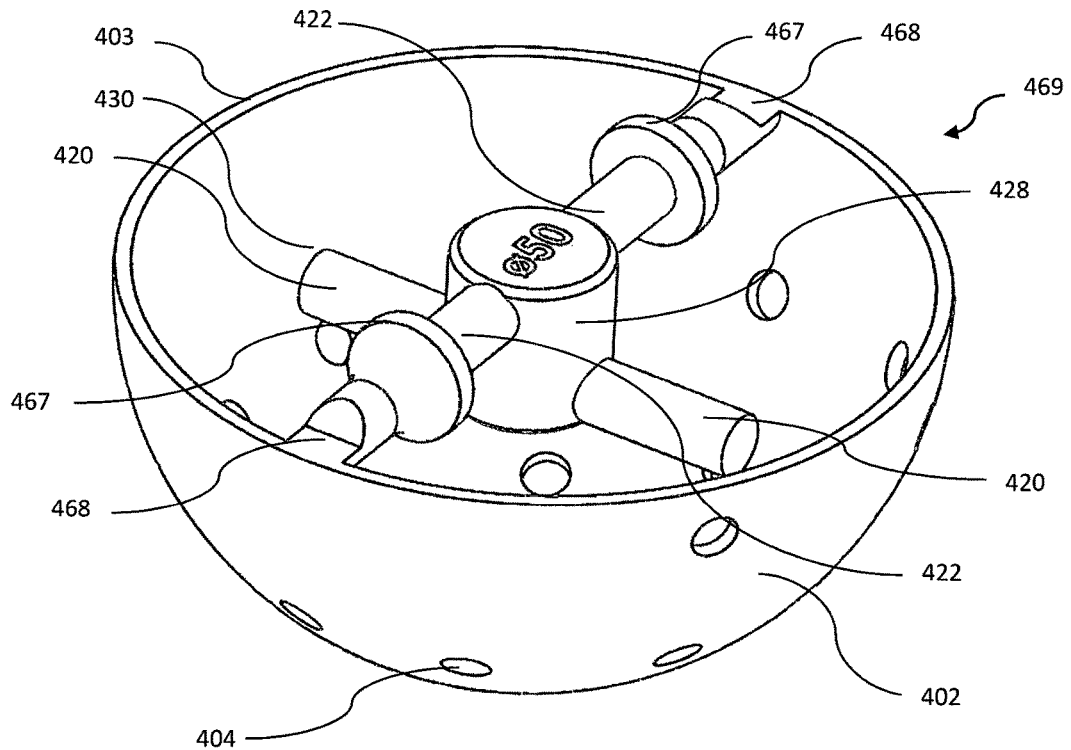
FIG. 4C is a perspective view of yet another variant of the acetabular reamer.

Now referring to FIGS. 4B and 4C, variant of the surgical reamer 466, 469 are illustrated. The first connecting bar 472, having a diameter D4, has two centering tapered features 467 having a larger diameter than the diameter D4. Both centering tapered features 467 have the same function as described above in FIG. 3. Optionally, the centering tapered features 467 can be removed as illustrated above in FIG. 1. Flats and tapers 468 are cut at both extremities of the connecting bar 472 to suppress sharp edges. The cutting size of the reamer 465 is marked or engraved on the center of the connecting bar 472. The half domed outer shell 402 of surgical reamer 466 includes cutting openings 404 which include sharp edges, and a circular rim(s) 403. In the variant in FIG. 4B, a torsional stabilization bar 406 is provided that extends from a first inner side wall 430 from one end to the other of the interior of the shell 402. Torsional stabilization bar 406 is spaced apart from connecting bar 472 and has a diameter of D5, and is connected to connecting bar 472 by connecting member 407. It is appreciated that the assembly that includes torsional stabilization bar 406, connecting bar 472 and connecting member 407 provide for increased structural stability of reamer 466, and in a method associated with the creation of the reamer 466 are injection molded in an injection molding process in one piece in one variant of the invention. In another variant of the invention, two or more injection molding processes are used to create the various components of the surgical reamer 466.

Now referring to FIG. 4C, another variant of a surgical reamer 469 is illustrated. In this variant of the surgical reamer 469, two spaced apart connecting bars 422 and 420 are connected to or form an integral part of the center circular member 428 (of course a variety of geometrical configurations of center circular member 428 are also contemplated, e.g. cubes, octagons, squares, etc.). Connecting bar 422 is attached to the inner wall 430 of the reamer shell 402. By way of contrast, connecting bar 420 is unconnected to inner wall 430 directly, but rather indirectly as illustrated. Similarly, connecting bars 420, 422 have diameters D7 and D8, and the diameters may be the same or different. As above, center circular member 428 has an engraving or marking thereon indicating the size of the aperture created by reamer 469. Both of the variants of FIGS. 4B, 4C provide for increased torsional and/or rotational stability of each of the reamers 468, 469.

It is appreciated that any of the surgical reamers described herein are used with a variety of reamer drivers, and reamer driver systems, and are configured to matingly and removeably attach to a variety of reamer driver systems.

Figure 5:
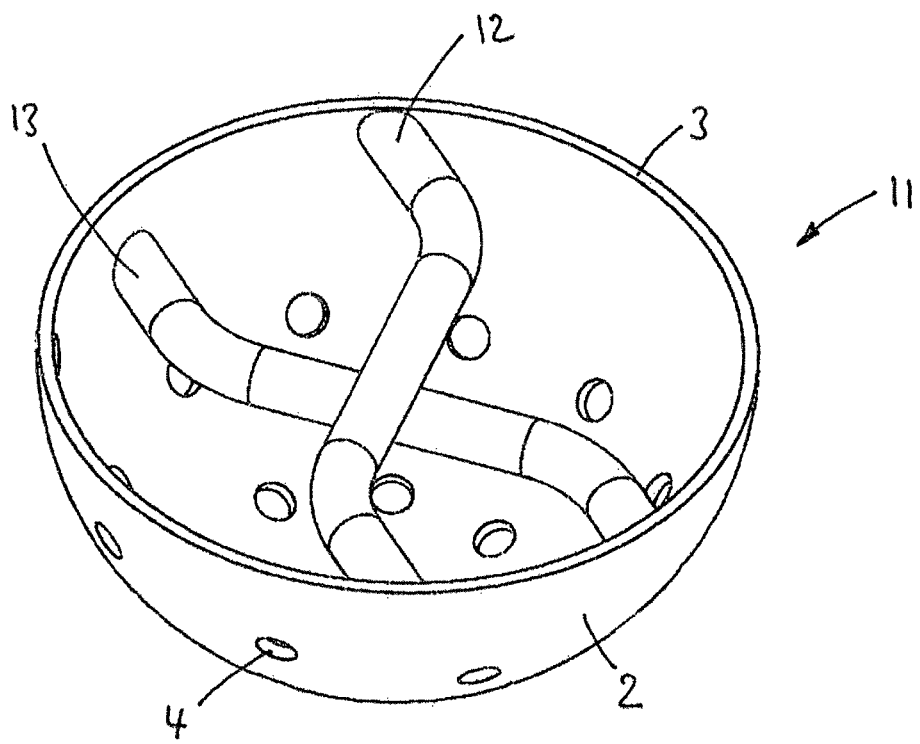
FIG. 5 is a perspective view of a less preferred variant of the acetabular reamer.

In a less preferred variant shown in FIG. 5, the acetabular reamer 11 comprises a first connecting bar 22 having a non-linear shape defined by a first end and a second end being parallel and a central portion being bent with an angle. The first connecting bar 22 is located on the inside surface of the domed shell 12, with its longitudinal axis being adjacent or closely adjacent to the rim 13 of the domed shell. A second connecting bar 23 having a non-linear shape defined by a first end and a second end being parallel and a central portion being bent with an angle is affixed on the inside surface of the domed shell 12. The second connecting bar 23 is positioned preferably parallel to the first connecting bar 22 in such way that the two bent central portions are perpendicular to each other. The second connecting bar 23 is spaced apart from the first connecting bar 22.

Figure 6:
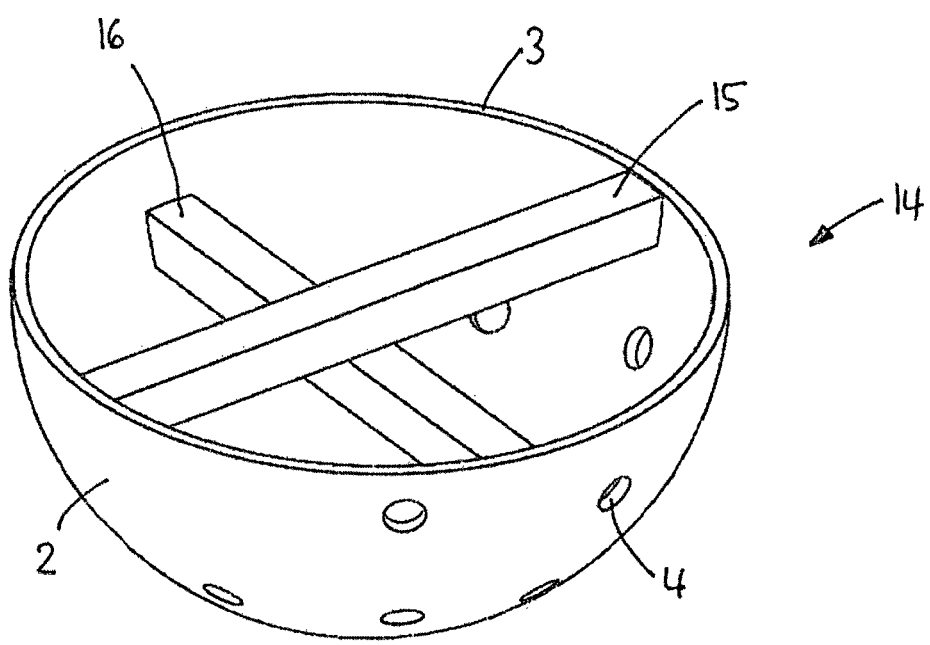
FIG. 6 is a perspective view of a different variant of the acetabular reamer.
Figure 7:
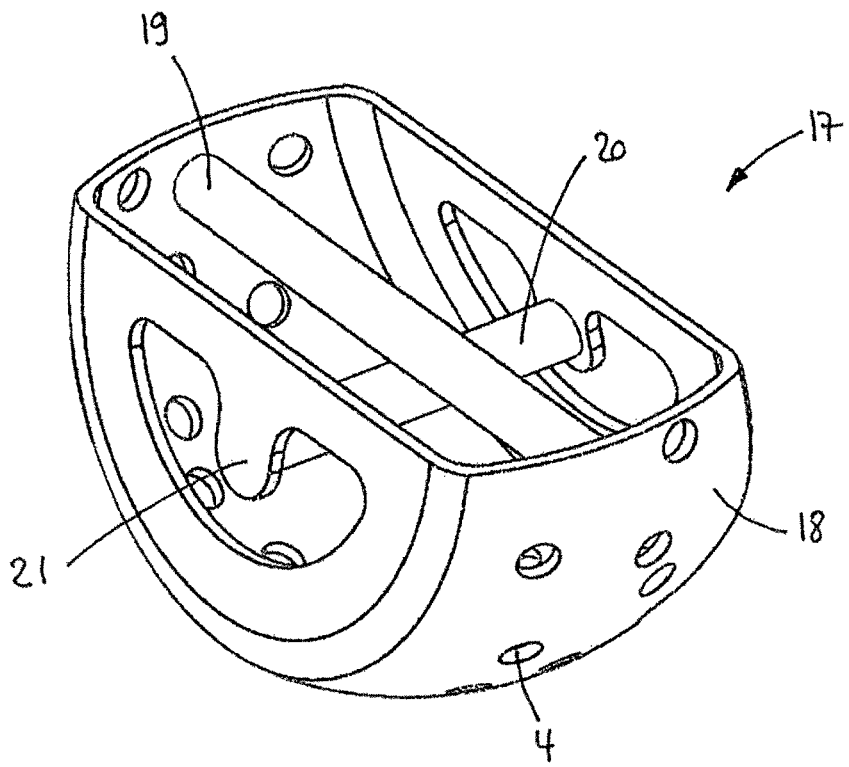
FIG. 7 is a perspective view of a minimal invasive acetabular reamer.

Now referring to FIG. 6 a different variant of the acetabular reamer 24 is shown were the cross-section of the connecting bars 25 and 26 are squared. A different variant of a minimal invasive acetabular reamer 27 is shown in FIG. 7. The domed shell 28 has two planar surfaces disposed symmetrically from a virtual plan coincident to the main axis of the reamer and intersecting the apex of the domed shell to form a wedge. The reduced section of the acetabular reamer allows insertion of the reamer through minimal openings. The first connecting bar 29 is located on the inside surface of the domed shell 12, with its longitudinal axis being adjacent or closely adjacent to the rim 13 of the domed shell and coincident with the virtual plan. A second connecting bar 30 is located on the inside surface of the tabs 31 disposed on the two planar surfaces of the domed shell 28. The second connecting bar 30 is positioned preferably perpendicular to the first connecting bar 29 and spaced apart from the first connecting bar 29.

Figure 8:
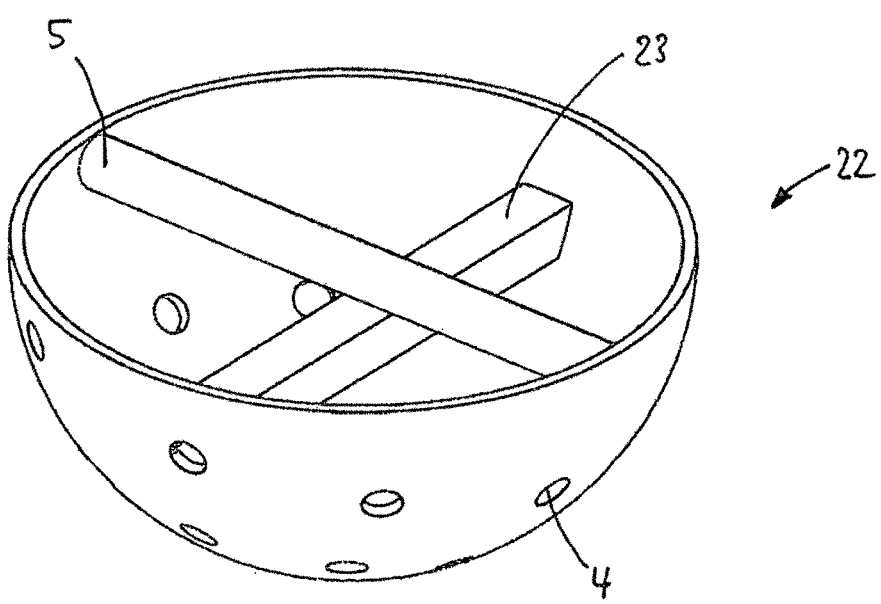
FIG. 8 is a perspective view of another variant of the acetabular reamer.
Figure 9:
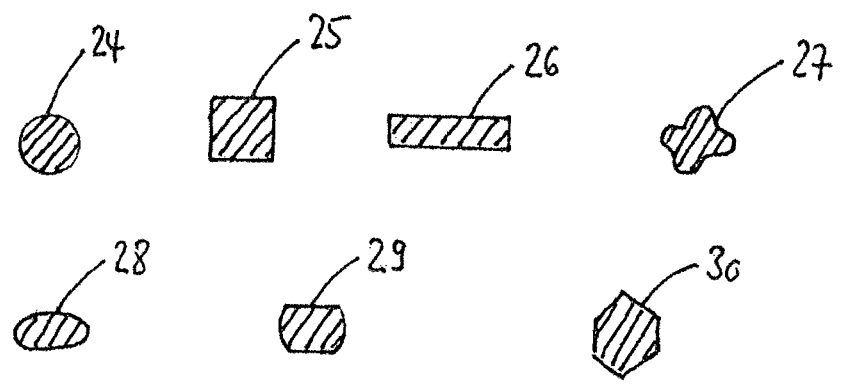
FIG. 9 is different cross-section shape of connecting bars of the acetabular reamer.

Still in a different variant 32 shown in FIG. 8, the cross-section of the second connecting bar 33 is square. As shown in FIG. 9, the cross-section of the first or the second or both connecting bars can be of various shapes like round 15a, 16a, square 15b, 16b, rectangular 15c, 16c, elliptical 15e, 16e, round with flats 15f, 16f, hexagonal 15g, 16g or any existing shape 15d, 16d. The connecting bars can be solid or hollow.

Figure 10A:
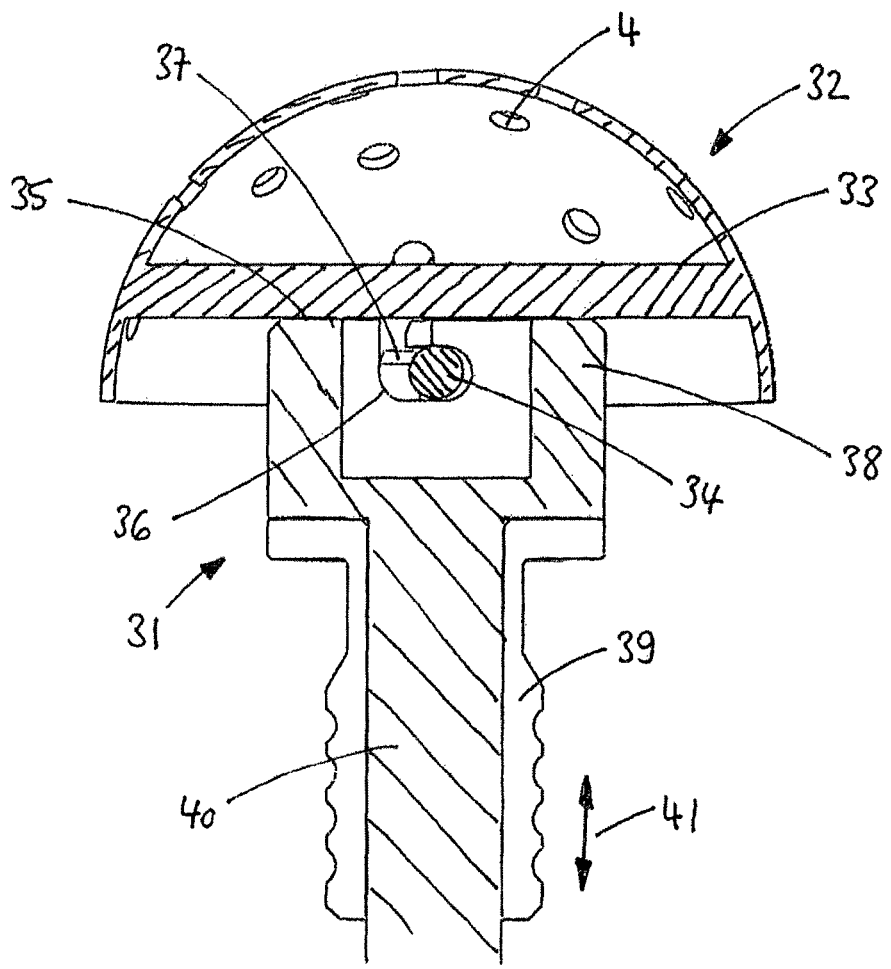
FIG. 10A is a cross-section view of a variant of the acetabular reamer connected to the preferred variant of a reamer driver.

Now referring to FIG. 10A, the acetabular reamer 42 of the present invention connected to a reamer driver 41. The reamer driver 41 has a main shank 50 having a longitudinal axis being parallel to the main axis of the reamer. The main shank 50 has a shank head 48 having two L-shaped openings 46 disposed 180° apart of each other for inserting the first connecting bar 44 of the reamer. A push-pull (51) sleeve 49 having two locking pins 47 slides on the main shank 50. When the push-pull sleeve 49 is placed in its upper position, the locking pins 47 passing through the shank head 48 close the entrance of the L-shaped openings 46 and locks the first connecting bar 44 inside the shank head 48. To avoid rocking and wiggling of the acetabular reamer once connected, the second connecting bar 43 sits on the front face 45 of the shank head. Once connected, rotation of the main shank 50 is transmitted to the acetabular reamer 42 through the first connecting bar 44. It will be understood that the L-shaped openings and the locking pins can be replaced by any other means, shapes or features allowing the connection of the connecting bar to the reamer driver. For example, the opening may be a simple U-shaped opening where an elastic clip is designed to retain the connecting bar inside the opening. Other combination of openings and locking mechanisms offering a connection may also be used. This applies to the other variants of FIGS. 10B and 13, for example.

Figure 10B:
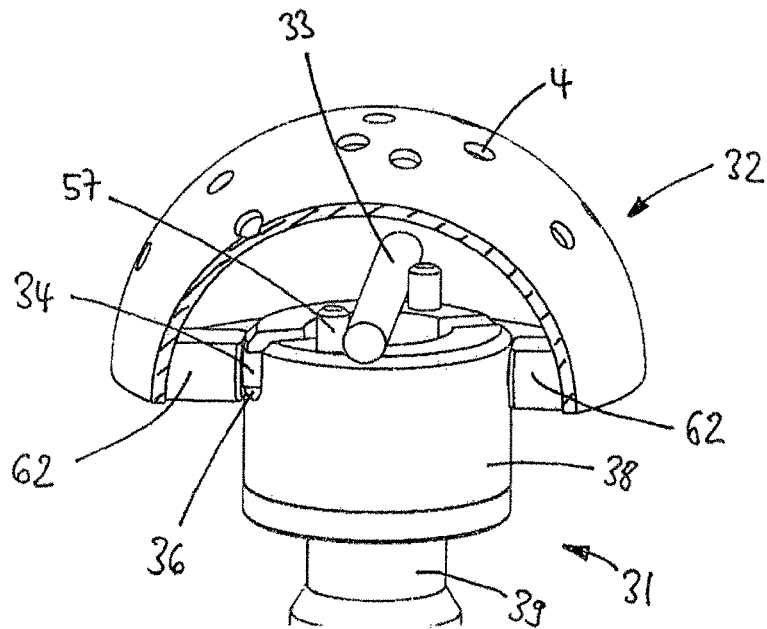
FIG. 10B is a different view of a variant of the acetabular reamer connected to the preferred variant of a reamer driver.

FIG. 10B illustrates a variant of FIG. 10A where at least one but preferably two pins 57 affixed to or being part of the shank head 48 are contacting the second connecting bar 43 in order to split the torque transmitted from the reamer driver to the acetabular reamer 42. Two centering features 62 of the first connecting bar 44 are symmetrically spaced apart from each other from the rotation axis of the domed shell and insure centering of the reamer once connected to the reamer driver. In a different variant, the pin 57 may be replaced by any features or openings made in the shank head 48 and having the same function.

Figure 11:
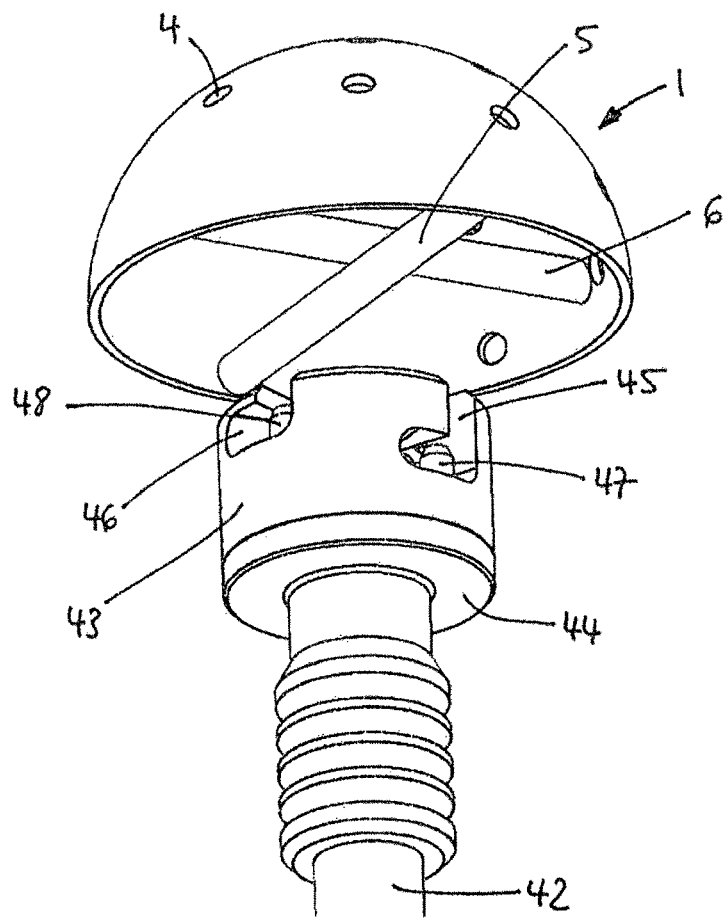
FIG. 11 is a perspective view of a variant of the acetabular reamer and a second variant of a reamer driver.

In a different variant shown in FIG. 11, the shank head 53 has a second set of two L-shaped openings 55 disposed 180° apart from each other and 90° apart from the first set of L-shaped openings 56. When coupling the reamer 11 to the reamer driver, the first connecting bar 15 goes into the second set of openings 55 and the second connecting bar 16 goes into the first set of openings 56. A push-pull sleeve 54 having four locking pins 57 and 58 slides on the main shank 52. When the push-pull sleeve 54 is placed in its upper position, the locking pins 57 and 58, passing through the shank head 53, close the entrance of the two sets of L-shaped openings 55 and 56 in order to lock the first and the second connecting bars inside the shank head 48.

Figure 12:
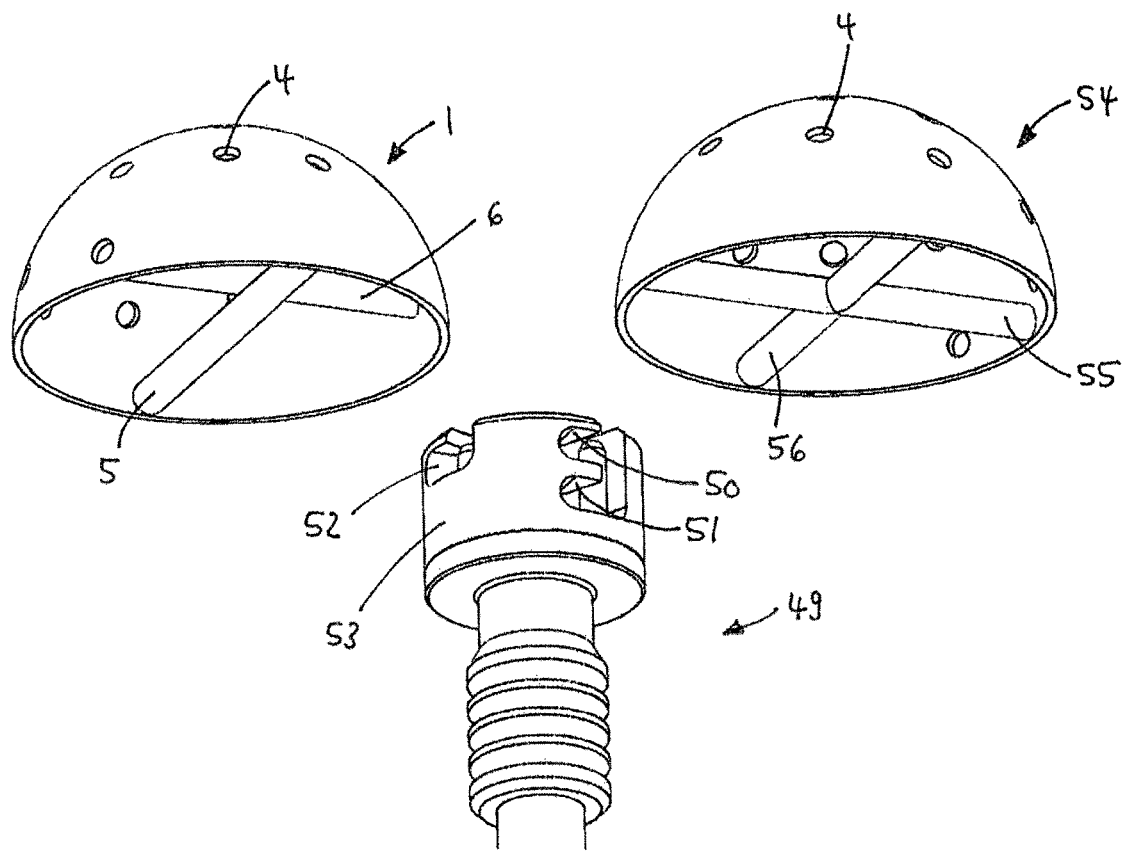
FIG. 12 is a perspective view of a variant of the acetabular reamer, a prior art variant of an acetabular reamer and a third variant of a reamer driver.

In a still different variant shown in FIG. 12, the shank head 64 of the reamer driver 59 has a second set of two L-shaped openings 63 disposed 180° apart from each other and 90° apart from the first set of L-shaped openings 60. A third set of two L-shaped openings 61 disposed 180° apart from each other and aligned below the first set of L-shaped openings 50 allows connection of different type of acetabular reamer. The acetabular reamer 10 has connecting bars according to the preferred variant of the present invention. The acetabular reamer 64 has two connecting bars 65 and 66 rigidly attached in its center. When coupling the acetabular reamer 10 to the reamer driver 59, the first connecting bar 15 goes into the third set of openings 61 and the second connecting bar 16 goes into the second set of openings 63. When coupling the acetabular reamer 64 to the reamer driver 59, the first connecting bar 65 goes into the second set of openings 63 and the second connecting bar 66 goes into the first set of openings 60.

Figure 13:
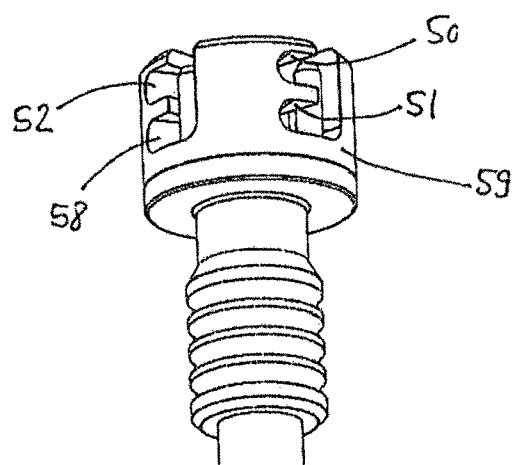
FIG. 13 is a perspective view of a fourth variant of a reamer driver.
Figure 14:
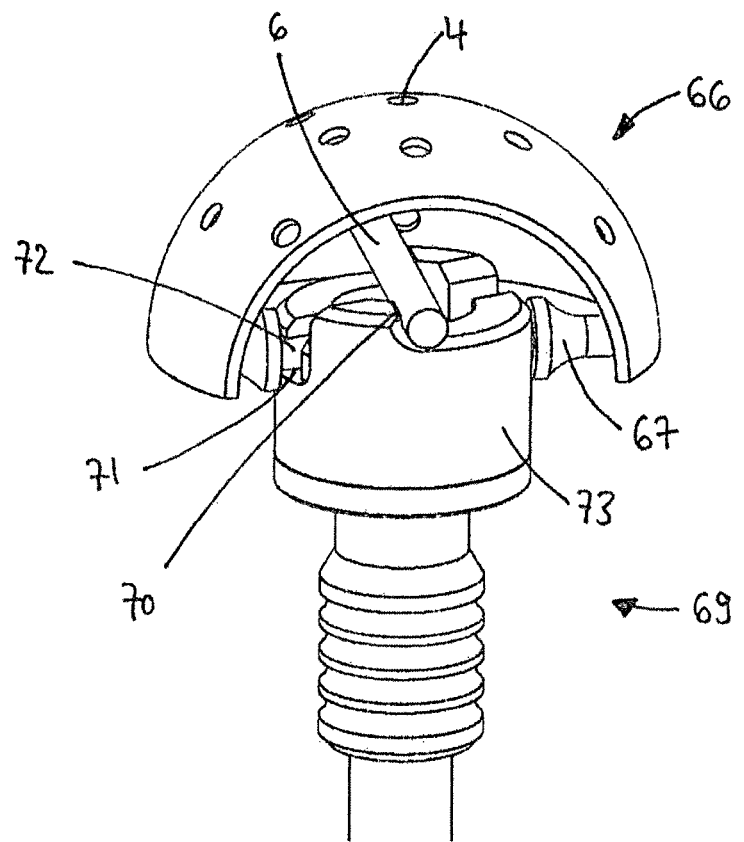
FIG. 14 is a perspective view of the preferred variant of the acetabular reamer and the second preferred variant of a reamer driver.

FIG. 13 shows an improved variant of FIG. 12 where a fourth set of L-shaped openings 68 disposed 180° apart from each other and aligned below the second set of L-shaped openings 63. This additional set of L-shaped openings allows the connection of the acetabular reamer 10 with an angular position offset by 90°. FIG. 14 shows a similar variant 19 to that of FIG. 10 where two faces 70 being part of the shank head 73 are contacting the second connecting bar 16 in order to split the torque transmitted from the reamer driver to the acetabular reamer 76. Two centering tapered features 67 of the first connecting bar 72 are symmetrically spaced apart from each other from the rotation axis of the domed shell and insure centering of the reamer once connected to the reamer driver.

The surgical reamer variants are used in a variety of mobile bearing hip and other joint replacement systems and various surgical protocols. By way of example, typical surgical protocols include one or more of the following steps: pre-operatively planning and evaluating the target area through X-ray or other imaging system evaluation, acetabular preparation by the release and removal of soft tissue to gain exposure for reaming and excision of the labrum and osteophytes for proper visualization of the bone anatomy and to improve ease of reaming, spherical reaming to prepare the acetabulum for restoration components, assessment of bone stock, level of interference and proper amount of under-reaming, trial evaluation of the restoration of the restoration cup following the reaming step, restoration cup implantation including assessment of the acetabulum and surrounding soft tissue prior to cup introduction, after cup implantation, insertion/head trial reduction, insert/head implantation, and reduction and closure, removal of cup, removal of insert and head unit. Of course other typical surgical protocols are also used with the surgical reamer of the present invention. Generally, use the reamer described herein to prepare the acetabular implant site includes the steps of hold the reamer steady and applying pressure in the same direction that the prosthesis will be implanted.

Kits including the reamer described here further include a variety of one or more optional accessories. These accessories include, by way of example, offset reamer handles, positioning assemblies, a variety of different diameter and length bone screws, a variety of different size liners, a variety of different size locking rings, a variety of sized shells, a variety of different size liner shells (e.g. polyethylene shells), and a variety of prosthesis implantation tools.

In yet an alternate variant, the surgical system is provided herein including the surgical reamer and variants described herein. The surgical system includes a surgical reamer driver, and surgical operating suite components, and the various combinations, and permutations of the surgical reamer described herein.

Additional features and functionality of the invention are described in the claims appended hereto. Such claims are hereby incorporated in their entirety by reference thereto in this specification and should be considered as part of the application as filed.

Multiple variations and modifications are possible in the variants of the invention described here. Although certain illustrative variants of the invention have been shown and described here, a wide range of changes, modifications, and substitutions is contemplated in the foregoing disclosure. While the above description contains many specific details, these should not be construed as limitations on the scope of the invention, but rather exemplify one or another preferred variant thereof. In some instances, some features of the present invention may be employed without a corresponding use of the other features. Accordingly, it is appropriate that the foregoing description be construed broadly and understood as being illustrative only, the spirit and scope of the invention being limited only by the claims which ultimately issue in this application.

What is claimed is:

1. A surgical reamer comprising: a continuous, fully hemispherical domed shell extending from the apex to the rim, a rotation axis, cutting teeth disposed around the domed shell wherein a first linear connecting bar having a first longitudinal axis and a first diameter is located on the inside surface of the domed shell, with its first longitudinal axis being adjacent or closely adjacent to the rim and wherein a second linear connecting bar having a second longitudinal axis and a second diameter is located on the inside surface of the domed shell and spaced apart by a distance from the first connecting bar, wherein an angle between the first longitudinal axis and the second longitudinal axis is 90 degrees or less, wherein at least a portion of a first cross-section of the first diameter is disposed below the rim and a second cross-section of the first diameter is disposed above the rim, and wherein a second cross-section of the second diameter is fully disposed below the rim and the first diameter.

2. The surgical reamer of claim 1, wherein the first connecting bar has two centering features, each one having a face that is symmetrically spaced apart with the other from the rotation axis of the domed shell.

3. The surgical reamer of claim 1, wherein the first connecting bar and the second connecting bar are connected together by a connecting member, wherein the connecting member is disposed in a plane other than a plane in which one of the connecting bars are disposed.

4. The surgical reamer of claim 1, wherein the space between the first and the second connecting bars is equal to the sum of the first and second diameters of the bars divided by two.

5. The surgical reamer of claim 1, wherein the second connecting bar is perpendicular to the first connecting bar.

6. The surgical reamer of claim 1, wherein the connecting bars are solid or hollow, having a cross-section being round, square, rectangular, elliptical, round with flats or hexagonal.

7. The surgical reamer of claim 1, wherein an item of information is displayed on the first connecting bar.

* * * * *